US00PP17230P2

(12) United States Plant Patent
Morum

(10) Patent No.: US PP17,230 P2
(45) Date of Patent: Nov. 21, 2006

(54) ***OENOTHERA* PLANT NAMED 'TURNER01'**

(50) Latin Name: *Oenothera speciosa*
Varietal Denomination: TURNER01

(76) Inventor: Lyn Angela Morum, 5 Godman Close, Aldwick, Bognor Regis, West Sussex PO21 4BJ (GB)

( * ) Notice: Subject to any disclaimer, the term of this patent is extended or adjusted under 35 U.S.C. 154(b) by 2 days.

(21) Appl. No.: 11/138,167

(22) Filed: May 25, 2005

(51) Int. Cl.
*A01H 5/00* (2006.01)

(52) U.S. Cl. ..... Plt./263
(58) Field of Classification Search ..... Plt./226, Plt./263
See application file for complete search history.

(56) References Cited

U.S. PATENT DOCUMENTS

PP16,393 P2 * 3/2006 Hofmann ..... Plt./263

OTHER PUBLICATIONS

UPOV ROM GTITM Computer Database, GTI Jouve Retrieval Software 2005/05 Citation for 'TURNER 01'.*

* cited by examiner

*Primary Examiner*—Wendy Haas

(57) ABSTRACT

A new cultivar of *Oenothera* plant named 'TURNER01', characterized by low spreading habit, deep-purple variagated leaves with green edges, and pink flowers that bloom from early spring through summer. In combination these traits set 'TURNER01' apart from all other existing varieties of *Oenothera* known to the inventor.

3 Drawing Sheets

Genus: *Oenothera*. Species: *speciosa*.
Denomination: TURNER01.

BACKGROUND OF THE INVENTION

The present invention relates to a new and distinct variety of evening primrose which may be grown as a perennial plant in regions where it is hardy and as an annual bedding plant in regions where it is tender. The new cultivar is known botanically as *Oenothera speciosa* and will be referred to hereinafter by the cultivar name 'TURNER01'.

The new cultivar 'TURNER01' was discovered in 2001 at a nursery in Barnham, West Sussex, England as a naturally occurring branch sport on an individual whole plant of *Oenothera speciosa* 'Siskiyou' (unpatented). The parent of 'TURNER01' is an individual plant of *Oenothera speciosa* 'Siskiyou'.

The inventor, who is an experienced propagator of perennial plants, discovered 'TURNER01' while taking cuttings from plants of *Oenothera speciosa* 'Siskiyou' for subsequent propagation and production. Whereas the foliage of *Oenothera speciosa* 'Siskiyou' is uniformly green in color, the leaves of the branch sport, 'TURNER01' were observed by the inventor to be deep purple in color. The inventor considered that the branch sport may have commercial potential if it could be propagated and found to reproduce true to type. In 2001, the inventor excised the branch sport from its parent plant and took a nodal cutting from the excised plant material. The nodal cutting was placed under mist on a heated bench, with bottom heat temperature of 21° Centigrade. The nodal cutting rooted and was transplanted into a 9 cm container and observed by the inventor. The inventor observed that the new plant possessed the characteristic dark purple foliage coloration of the originally discovered branch sport, 'TURNER01'.

Since 2001, the inventor has carried out annual cycles of asexual propagation and observed that in each generation the new *Oenothera* cultivar named 'TURNER01' has remained stable and has reproduced true to type by asexual reproduction.

The new cultivar 'TURNER01' is characterized by dense mounding form, low spreading habit, deep purple variegated leaves with green edges, and pink flowers that are typical of the species. 'TURNER01' is vigorous and spreads freely by rhizomes. Foliage color is pronounced during colder months, and 'TURNER01' goes dormant in winter when planted in cold climates.

The closest comparison plant is the parent *Oenothera speciosa* 'Siskiyou'. The new variety 'TURNER01' is distinguishable from the parent plant by habit and foliage color. The parent exhibits solid green leaves. In deep shade and after flowering the leaf color of 'TURNER01' fades, however with fertilization, increased sunlight, and pruning, foliage resumes the deep-purple color with green edges.

SUMMARY OF THE INVENTION

The following traits have been repeatedly observed and represent the distinguishing characteristics of the new variety 'TURNER01'. In combination these traits set 'TURNER01' apart from all other *Oenothera* known to the inventor. 'TURNER01' has not been tested under all possible conditions and phenotypic differences may be observed with variations in environmental, climatic and cultural conditions, however, without any variance in genotype.

1. *Oenothera speciosa* 'TURNER01' exhibits low spreading habit.
2. *Oenothera speciosa* 'TURNER01' blooms from early spring to summer exhibiting pink flowers that are typical of the species.

3. *Oenothera speciosa* 'TURNER01' exhibits deep purple variegated leaves with green edges.
4. *Oenothera speciosa* 'TURNER01' exhibits pronounced foliage color during colder months.
5. *Oenothera speciosa* 'TURNER01' is suitable for use in borders, containers, and a groundcover in the landscape.
6. *Oenothera speciosa* 'TURNER01' exhibits dense mounding form.
7. The cultural requirements for *Oenothera speciosa* 'TURNER01' are fertile well-draining soil, full sun, and minimal to moderate water.
8. *Oenothera speciosa* 'TURNER01' is vigorous, spreading freely by rhizomes.
9. *Oenothera speciosa* 'TURNER01' goes dormant in winter when planted in cold climates.
10. *Oenothera speciosa* 'TURNER01' can be propagated by the methods of softwood cuttings, tissue culture, or division.
11. *Oenothera speciosa* 'TURNER01' has been found to be hardy and to survive in temperatures of minus 10° Centigrade.
12. *Oenothera speciosa* 'TURNER01' is 20 cm. in height and 40 cm. in width at maturity.

BRIEF DESCRIPTION OF THE DRAWINGS

The accompanying color drawings labeled

The drawing labeled FIG. 1 depicts a 10 months old plant of 'TURNER01' just prior to budding. The plant is growing in a 1 liter container, and has been grown out of doors at the inventor's nursery in Sussex, England. The plant was potted as a small rooted plug in the previous fall.

The drawing labeled FIG. 2 depicts a close-up view of the foliage of 'TURNER01' showing its characteristic dark-purple coloration and green margin.

Figure 3:
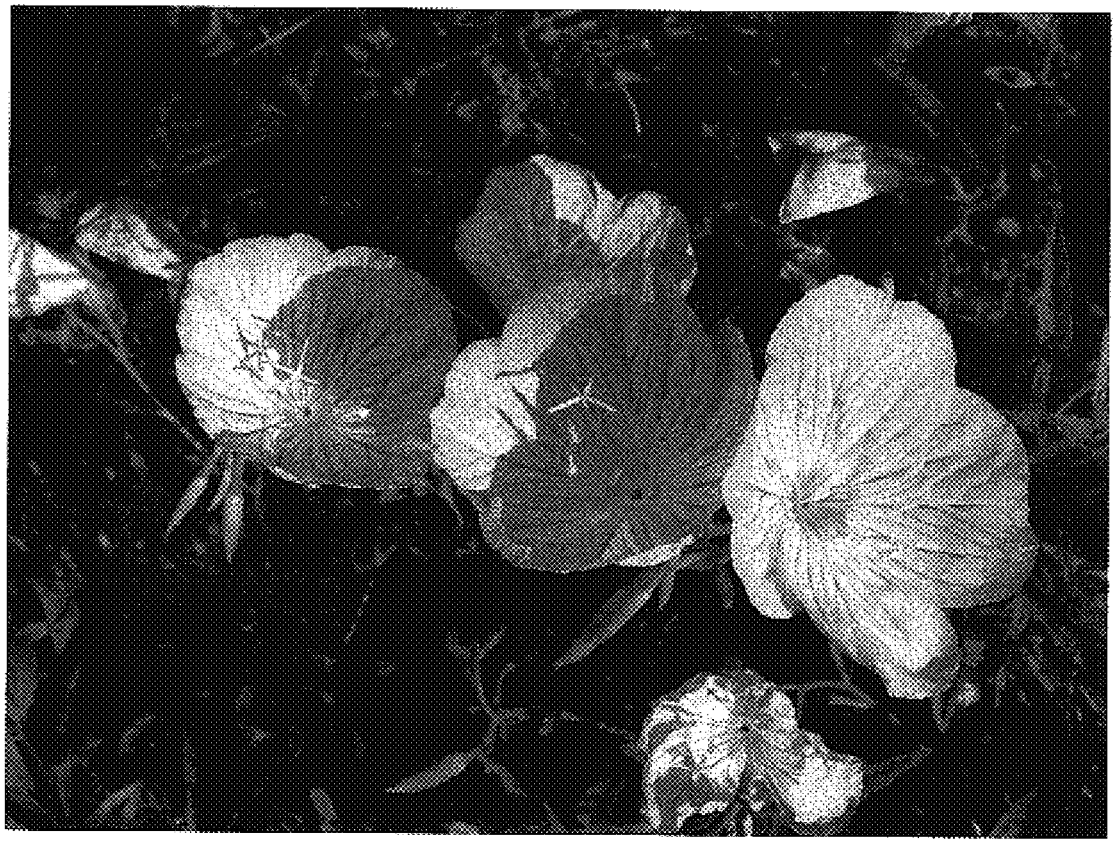

The drawing labeled as FIG. 3 depicts a close up view of the buds and flowers of 'TURNER01'. The buds and flowers of 'TURNER01' are typical of the parent variety, *Oenothera speciosa* 'Siskiyou'.

Figure 1:
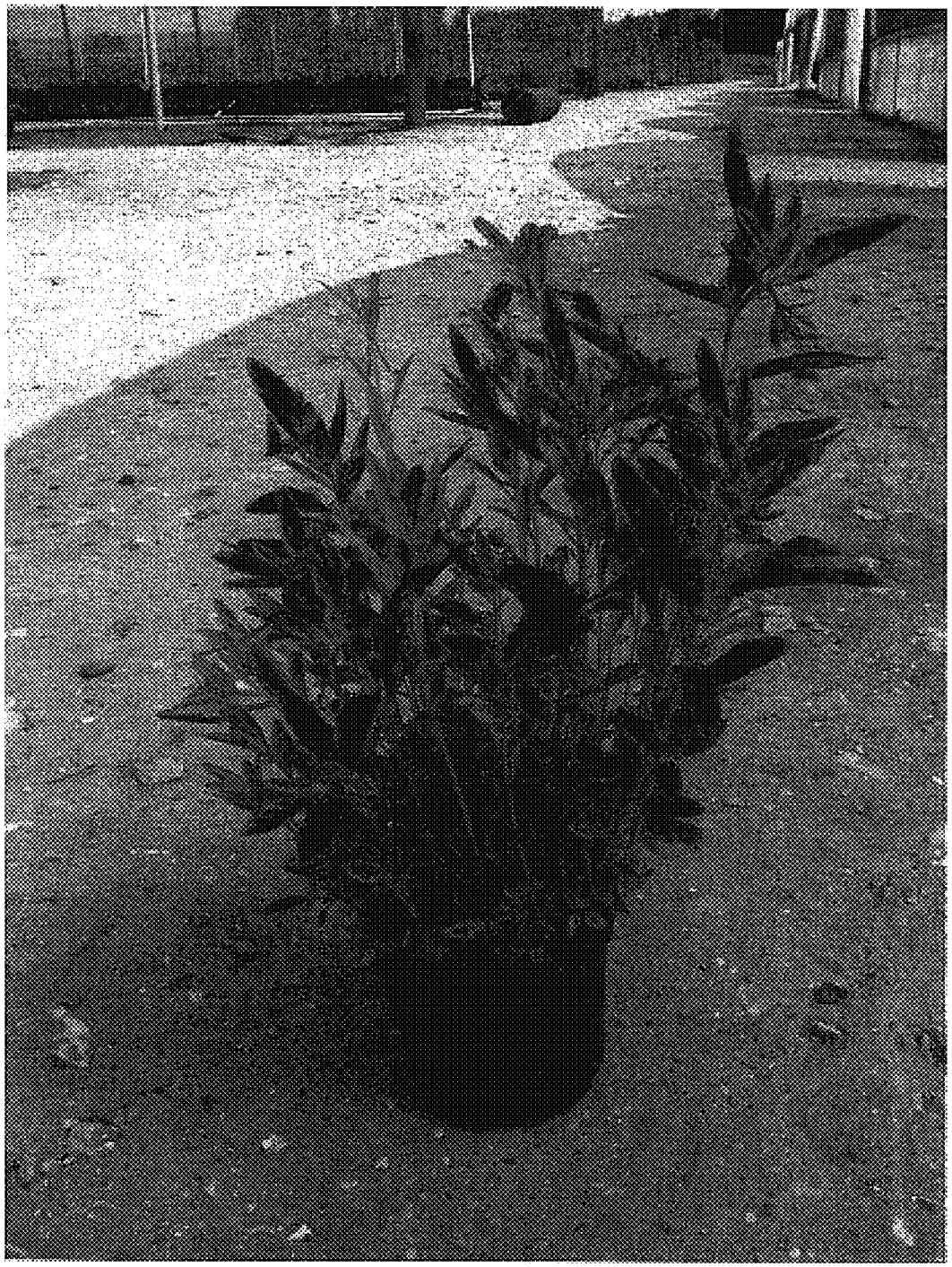
FIG. 1, FIG. 2 and FIG. 3 illustrate the overall appearance of the new *Oenothera* cultivar 'TURNER01' showing the colors as true as it is reasonably possible to obtain in colored reproductions of this type. Colors in the drawings may differ from the color values cited in the detailed botanical description, which accurately describe the actual colors of the new variety 'TURNER01'.
Figure 2:
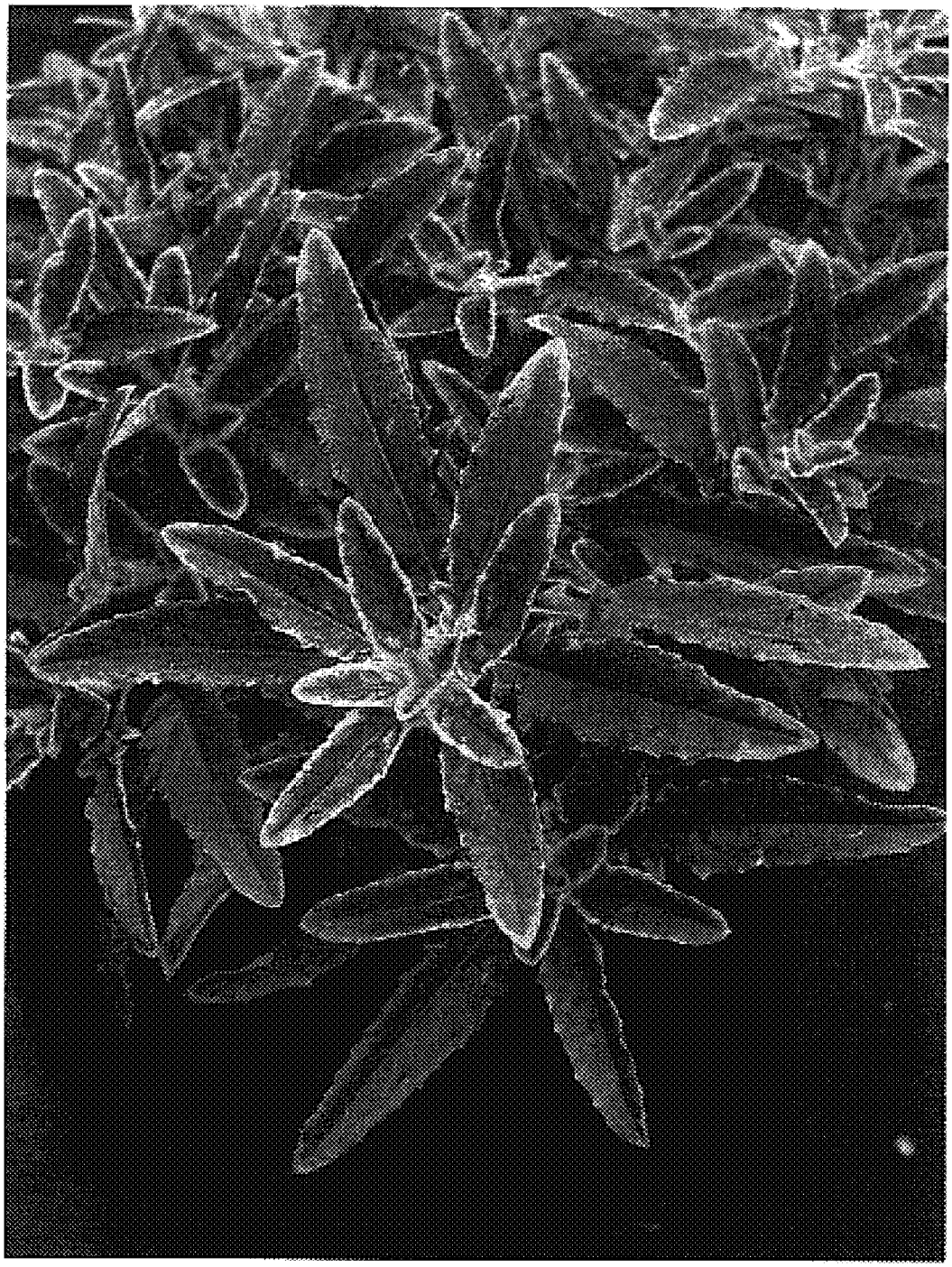

FIG. 1, FIG. 2 and FIG. 3 were made using conventional techniques and although colors may appear different from actual colors due to light reflectance they are as accurate as possible by conventional photography.

BOTANICAL DESCRIPTION OF THE PLANT

The following is a detailed description of the new *Oenothera* plant named 'TURNER01'. Data was collected in Arroyo Grande Calif. from 6-month-old plants grown out-of-doors in 2-liter containers. The color determinations are in accordance with the 2001 edition of The Royal Horticultural Society's Colour Chart, except where general color terms of ordinary dictionary significance are used.

Botanical classification: *Oenothera speciosa* 'TURNER01'.
Genus: *Oenothera*.
Species: *speciosa*.
Denomination: TURNER01.
Common name: Evening primrose.
Commercial classification: Perennial and annual, according to planting environment.
Plant form: Dense mound.
Plant use: Suitable for use in borders, containers, or in the landscape.
Cultural requirements: Fertile well-draining soil, full sun, and minimal to moderate water.
Root system: Fine and fibrous.
Vigor: Vigorous, spreading freely by rhizomes.
Parentage: *Oenothera speciosa* 'TURNER01' was discovered as a naturally occurring branch sport on an invidual whole plant of the following parent:
*Parent plant.*—*Oenothera speciosa* 'Siskiyou'.
Plant description:
*Seasonal interest.*—Flowers bloom in April, May, June, and the deep-purple foliage color is pronounced duing colder months.
*Plant habit.*—Low spreading habit.
*Height.*—20 cm. in height at maturity.
*Width.*—40 cm. in width at maturity.
*Hardiness.*—At least hardy to minus 10° Centigrade; hardy in USDA zones 8 and warmer.
*Propagation.*—Propagation is accomplished using vegetative cuttings, division or tissue-culture.
*Time to develop roots.*—1–2 weeks are needed for initial cuttings to develop roots.
*Temperature for rooting.*—Recommended air temperature for rooting is 10–25° Centigrade.
*Crop time.*—12 weeks are needed to produce a finished 1-liter commercial container plant from a rooted cutting.
*Disease susceptibility.*—'TURNER01' is susceptible to *Botrytis* spp.
*Disease resistance.*—'TURNER01' exhibits no known resistance to disease, known to the inventor.
*Growing problems.*—Foliage color is reduced in full shade, after flowering, and with low soil fertility.
*Growing requirements.*—'TURNER01' exhibits its characteristics most fully when grown in full sun, pruned after flowering, and fertilized to maintain deep purple coloration to the foliage.
Stems:
*Branching.*—Basal rosette.
*Stem shape.*—Cylindrical.
*Stem color.*—Individual colors 165A, 165B and 138B are present on an individual stem.
*Stem dimensions.*—Spreading stems range from 12 cm. in length and 0.25 cm. in diameter, to 6 cm. in length and 2 mm. in diameter.
*Stem surface.*—Pubescent.
*Internode length.*—1.25 cm. between nodes.
Foliage:
*Leaf shape.*—Individual leaf shape ranges from elliptic to elongated lyrate.
*Leaf division.*—Individual leaf division ranges from simple to pinnatilobate.
*Leaf apex.*—Leaf apex on an individual leaf ranges from acute to rounded.
*Leaf base.*—Slender attenuate.
*Stipules.*—None observed.
*Leaf margins.*—Leaf margins are mildly dentate.
*Leaf attachment.*—Sessile and petiolate leaf attachments are individually present on an individual plant.

*Leaf arrangement.*—Leaf arrangement is a combination of opposite and whorled on individual stems.
*Leaf surfaces* (*adaxial and abaxial surfaces*).—Slightly puberulent.
*Leaf width.*—Leaves range from 0.75 cm. to 1.25 cm. in width.
*Leaf length.*—Leaves range from 2.50 cm. to 7.50 cm. in length.
*Petiole shape.*—Cylindrical.
*Petiole color.*—189A.
*Petiole dimensions.*—1 cm. in length and 0.50 mm. in width.
*Leaf color, mature leaves,* (*adaxial surface*).—Predominantly dark purple, 187A, except for apical margin up to 2 mm in width, green 143A.
*Leaf color, new and recently emerged leaves,* (*adaxial surface*).—Dark purple, 187A, except for entire margin up to 2 mm in width, green 143A.
*Leaf color* (*abaxial surface*).—191A.
*Venation pattern.*—Pinnate.
*Vein color* (*adaxial surfaces*).—187C at leaf base and extending approximately to center of leaf; tending to same color as leaf adaxial surface towards apex, namely 187A or 143A in region of green apical margin.
*Vein color* (*abaxial surfaces*).—194C.
*Fragrance.*—None observed.

Flowers:
*Bloom period.*—Early spring to summer.
*Inflorescence type.*—Solitary axillary flower.
*Quantity of buds.*—Number ranges from 10 to 30 individual buds on an individual plant.
*Quantity of flowers.*—Number ranges from 48–50 individual flowers on an individual plant.
*Flower shape.*—Funnelform.
*Flower dimensions.*—5 cm. in diameter and 2 cm. in depth.
*Corolla tube depth.*—5 mm. in depth.
*Persistent or self-cleaning.*—Persistent.
*Flower aspect.*—Flowers face upward and outward.
*Bud dimensions.*—Bud dimensions are 2 mm. in width and 10 mm. in length.
*Bud shape.*—Spindle-shaped.
*Bud color.*—138A.
*Bud surface.*—Puberulent.
*Bud apex.*—Acute.
*Calyx color.*—144B.
*Sepals.*—Three in number.
*Sepals fused or unfused.*—Sepals are unfused.
*Sepal color* (*abaxial and adaxial surfaces*).—144B.
*Sepal dimensions.*—Sepal dimensions are 3 cm. in length and 0.75 cm. in width.
*Sepal apex.*—Acute.
*Sepal base.*—Truncate.
*Sepal shape.*—Lanceolate.
*Sepal margin.*—Entire.
*Sepal surface* (*abaxial surface*).—Puberulent.
*Sepal surface* (*adaxial surface*).—Puberulent.
*Sepal surface appearance* (*abaxial surface*).—Matte.
*Sepal surface appearance* (*adaxial surface*).—Matte.
*Petals.*—Four in number.
*Petals fused or unfused.*—Petals unfused.
*Petal color* (*adaxial surface*).—Individual colors 75B and 75A, 155B, and 151B are present on an individual petal.
*Petal color* (*abaxial surface*).—Individual colors 75B, 75A, 155B, and 151B are present on an individual petal.
*Petal shape.*—Obdeltoid.
*Petal margin.*—Entire.
*Petal apex.*—Emarginated.
*Petal base.*—Cuneate.
*Petal surfaces* (*adaxial and abaxial surfaces*).—Glabrous.
*Petal dimensions.*—Petal dimensions are 2.50 cm. in length and 3 cm. in width.
*Peduncle dimensions.*—Peduncle dimensions are 2 cm. in length and 2 mm. in diameter.
*Peduncle shape.*—Cylindrical.
*Peduncle color.*—144B.
*Peduncle surface.*—Puberulent.
*Flower fragrance.*—None observed.

Reproductive organs:
*Stamens.*—Eight stamens in number.
*Stamen color.*—155B.
*Stamen dimensions.*—Stamen dimensions are 14 mm. in length and 0.50 mm. in diameter.
*Anther color.*—164A.
*Anther dimensions.*—Anther dimensions are 4 mm. in length and 0.50 mm. in width.
*Quantity of pollen.*—Moderate amount of pollen present.
*Color of pollen.*—161A.
*Pistil.*—One in number.
*Pistil dimensions.*—Pistil dimensions are 18 mm. in length and 1.50 mm. in width.
*Pistil color.*—155B.
*Pistil shape.*—Filament.
*Pistil surface.*—Glabrous.
*Stigma shape.*—Stellate.
*Stigma diameter.*—9 mm. in diameter.
*Stigma color.*—155B.
*Ovary position.*—Inferior.
*Ovary color.*—144A.
*Ovary shape.*—Elongated oval.
*Ovary dimensions.*—Ovary dimensions are 9 mm. in length and 4 mm. in diameter.

Seed production: No seed production has been observed to date.

It is claimed:

1. A new and distinct cultivar of *Oenothera* plant named 'TURNER01' as described and illustrated.

* * * * *